(12) United States Patent
Ishii et al.

(10) Patent No.: US 6,399,806 B1
(45) Date of Patent: Jun. 4, 2002

(54) PROCESS FOR PRODUCING BINAPHTHOL BISTRIFLATE

(75) Inventors: Akihiro Ishii; Mikio Ujiie; Yokusu Kuriyama, all of Saitama; Mitsuru Tanuma, Chiba, all of (JP)

(73) Assignee: Central Glass Company Limited, Ube (JP)

( * ) Notice: Subject to any disclaimer, the term of this patent is extended or adjusted under 35 U.S.C. 154(b) by 0 days.

(21) Appl. No.: 09/697,683

(22) Filed: Oct. 27, 2000

(30) Foreign Application Priority Data

Oct. 28, 1999 (JP) .............................. 11-307772

(51) Int. Cl.$^7$ .......................................... C07C 303/00
(52) U.S. Cl. .......................................... 558/46
(58) Field of Search .......................................... 558/46

(56) References Cited

U.S. PATENT DOCUMENTS 5,399,771 A  3/1995  Cai et al. .................... 568/17

FOREIGN PATENT DOCUMENTS

WO   WO 99/36397   7/1999

OTHER PUBLICATIONS

Vondenhof et al., "Sulfonic Acid Esters from 1.1'–Binaphthalene as Axially Chiral Photosensitizers", Tetrahedron Letters, vol. 31 No. 7 (1990), pp. 985–988.

Martin (Editor), "Organic Syntheses", vol. 76, pp. 6–11.

*Primary Examiner*—Floyd D. Higel
*Assistant Examiner*—Ebenezer Sackey
(74) *Attorney, Agent, or Firm*—Crowell & Moring LLP

(57) ABSTRACT

A process for producing a binaphthol bistriflate, 2,2'-bis(trifluoromethanesulfonyloxy)-1,1'-binaphthyl, includes reacting 1,1'-bi-2-naphthol with trifluoromethanesulfonyl fluoride, in a polar solvent, in the presence of an organic base. The reaction proceeds quickly at a low temperature by using a polar solvent as the reaction solvent, while the reaction pressure does not become high. The polar solvent is preferably at least one selected from N,N-dimethylformamide, N,N-dimethylacetoamide, 1-methyl-2-pyrrolidinone, and acetonitrile.

20 Claims, No Drawings

PROCESS FOR PRODUCING BINAPHTHOL BISTRIFLATE

BACKGROUND OF THE INVENTION

The present invention relates to a binaphthol bistriflate, 2,2'-bis(trifluoromethanesulfonyloxy)-1,1'-binaphthyl. This compound is useful as a precursor of 2,2'-bis(diphenylphosphino)-1,1'-binaphthyl (BINAP), which is an important chiral ligand for catalytic asymmetric synthesis.

Each of Tetrahedron Letters, Vol. 31, No. 7, pp. 985–988, 1990, U.S. Pat. No. 5,399,771 and Organic Syntheses, Vol. 76, pp. 6–11 discloses a process for producing binaphthol bistriflate by reacting binaphthol with trifluoromethanesulfonic anhydride in the presence of an organic base.

WO 99/36397 discloses a process for producing binaphthol bis(perfluoroalkanesulfonate) derivatives, which are precursors of BINAP derivatives. In this process, binaphthol derivatives are reacted with a perfluoroalkanesulfonyl halide, $C_nF_{2n+1}SO_2X$, where n is an integer of 4–10 and X=F or Cl, or a perfluoroalkanesulfonic anhydride, $(C_nF_{2n+1}SO_2)_2O$, where n is an integer of 4–10, in the presence of an organic base.

As mentioned above, trifluoromethanesulfonic anhydride is used as a trifluoromethanesulfonylation agent for producing a binaphthol bistriflate. This anhydride is produced by obtaining trifluoromethanesulfonyl fluoride through electrolytic fluorination and then by hydrolyzing the trifluoromethanesulfonyl fluoride into trifluoromethanesulfonic acid, followed by dehydrocondensation, as follows.

$$CF_3SO_2F \rightarrow CF_3SO_3H \rightarrow (CF_3SO_2)_2O$$

The molecule of trifluoromethanesulfonic anhydride contains two trifluoromethanesulfonyl groups. However, only one of these groups is introduced into binaphthol, since the other group acts as the leaving group ($TfO^- = CF_3SO_3^-$). Therefore, trifluoromethanesulfonyl fluoride is superior to trifluoromethanesulfonic anhydride as a trifluoromethanesulfonylation agent. It is, however, very difficult to handle trifluoromethanesulfonyl fluoride, since this compound (boiling point: −20° C.) is highly volatile at normal temperature and normal pressure. In connection with this, WO 99/136397 discloses a perfluoro-1-butanesulfonylation at normal temperature and normal pressure using a low volatile perfluoroalkanesulfonylation agent, such as perfluoro-1-butanesulfonyl fluoride (boiling point: 64° C.), without using a special reaction apparatus such as pressure-proof reaction vessel. However, the introduction of a leaving group having many fluorine atoms is disadvantageous from the viewpoint of atom economy, since the final object is to synthesize BINAP derivatives.

SUMMARY OF THE INVENTION

It is an object of the present invention to provide a process for producing a binaphthol bistriflate, which does not require a special reaction apparatus such as a pressure-proof reaction vessel, although the process employs trifluoromethanesulfonyl fluoride, which is highly volatile at normal temperature (e.g., room temperature) and normal pressure (e.g., atmospheric pressure).

According to the present invention, there is provided a process for producing a binaphthol bistriflate represented by the formula (1). This process comprises reacting a binaphthol represented by the formula (2) with trifluoromethanesulfonyl fluoride, in a polar solvent, in the presence of an organic base.

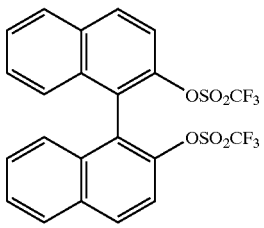

(1)

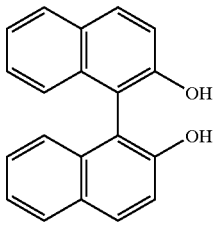

(2)

DESCRIPTION OF THE PREFERRED EMBODIMENTS

The inventors unexpectedly found that the reaction proceeds quickly at a low temperature by using a polar solvent as the reaction solvent, while the reaction vessel's pressure does almost not increase. Therefore, the process of the invention does not require a special apparatus such as a pressure-proof reaction vessel.

Binaphthol is a starting material in the process of the invention. This compound may be R-form, S-form or racemate in configuration. The racemization does not occur in the reaction. Therefore, it is possible to obtain a binaphthol bistriflate of R-form, S-form or racemate by suitably selecting stereoisomer of the binaphthol.

Trifluoromethanesulfonyl fluoride is used in the reaction as a trifluoromethanesulfonylation agent. This fluoride is in an amount preferably of at least 2 moles, more preferably 2–10 moles, still more preferably 2–5 moles, per mol of the binaphthol.

Nonlimitative examples of the organic base used in the reaction are trimethylamine, triethylamine, diisopropylethylamine, tri-n-propylamine, tri-n-butylamine, dimethyllaurylamine, dimethylaminopyridine, N,N-dimethylaniline, dimethylbenzylamine, 1,8-diazabicyclo(5,4,0)undecene-7, 1,4-diazabicyclo(2,2,2)octane, pyridine, 2,4,6-trimethylpyridine, pyrimidine, pyridazine, 3,5-lutidine, 2,6-lutidine, 2,4-lutidine, 2,5-lutidine, and 3,4-lutidine. Of these, trimethylamine, triethylamine, diisopropylethylamine, and tri-n-propylamine are preferable. In particular, triethylamine is more preferable. The amount of the organic base used in the reaction is preferably at least 2 moles, more preferably 2–10 moles, still more preferably 2–5 moles, per mol of the binaphthol.

Nonlimitative examples of the polar solvent used in the reaction are N,N-dimethylformamide (DMF), N,N-diethylformamide, N,N-dimethylacetoamide, 1-methyl-2-pyrrolidinone, 1,3-dimethyl-2-imidazolidinone, hexamethylphosphoric triamide, dimethyl sulfoxide, acetonitrile ($CH_3CN$), propionitrile, and benzonitrile. Of these, N,N-dimethylformamide, N,N-dimethylacetoamide, 1-methyl-2-pyrrolidinone, and acetonitrile are preferable. In particular, N,N-dimethylformamide and acetonitrile are more preferable. It is optional to use one of these compounds or a mixture of at least two of these in the reaction.

As stated above, the gist of the invention is to use polar solvent as the reaction solvent. An advantageous effect of the use of polar solvent is discussed in detail as follows. In case of using a highly volatile reagent in a reaction, it is generally important to quickly proceed the reaction at as low a reaction temperature as possible, With this, it becomes possible to minimize load to the reaction vessel in pressure. In other words, it becomes unnecessary to use a special reaction vessel such as pressure-proof reaction vessel. The results of the after-mentioned Examples 1–4 and Comparative Examples 1–2 are summarized in Table with respect to conversion of the reaction.

TABLE

| Reaction Condition | Comparative Solvent $CH_2Cl_2$ | Polar Solvent $CH_3CN$ | Polar Solvent DMF |
|---|---|---|---|
| −30° C. · 1 hr | Conversion: 23% (Com. Ex. 1) | Conversion: 73% (Example 1) | Conversion: 85% (Example 2) |
| −30° C. → 0° C. · 1 hr | Conversion: 73% (Com. Ex. 2) | Conversion: <99% (Example 3) | Conversion: <99% (Example 4) |

As shown in Table, methylene chloride ($CH_2Cl_2$) was used as a comparative solvent in Comparative Examples 1 and 2; methylene chloride is used as the most preferable reaction solvent in WO 99136397. It is understood from Table that the reaction proceeds quickly at low temperature by using polar solvent. The temperature of the reaction mixture was maintained at −30° C. for 1 hr in Examples 1 and 2. In contrast, it was increased from −30° C. to 0° C. and maintained at 0° C. for 1 hr in Examples 3 and 4. Even in Examples 3 and 4, the reaction vessel's pressure did almost not increase during the reaction, since most of the trifluoromethanesulfonyl fluoride was already consumed in the course of the temperature increase toward 0° C. Therefore, it was not necessary to use a special apparatus, such as a pressure-proof reaction vessel, is even in Examples 3 and 4. The reason why the reaction proceeded quickly at low temperature can be that the solubility of binaphthol (particularly its racemate which is less soluble in solvent) at low temperature improved remarkably by using polar solvent and that the rate of the trifluoromethanesulfonylation itself was accelerated by using polar solvent.

It suffices that the amount of polar solvent used in the reaction is in an amount sufficient for dissolving therein binaphthol in an amount sufficient for quickly proceeding the reaction at low temperature. Its amount is preferably from b 1to 10 liters, more preferably from 1.5 to 5 liters, per mol of binaphthol.

The reaction temperature is not particularly limited so long as it is in a range of from a first temperature, at which trifluoromethanesulfonyl fluoride (boiling point: −20° C.) can be introduced in liquid state, to a second temperature, at which the reaction vessel's pressure does not become too high. The reaction temperature is preferably from −60 to 10° C., more preferably from −50 to 0° C.

It is possible to obtain a crude product of the binaphthol bistriflate by conducting a conventional post-treatment after the reaction. According to need, it is possible to obtain the binaphthol bistriflate of high purity by conducting a purification such as purification with activated carbon, recrystallization or column chromatography.

The following nonlimitative examples are illustrative of the present invention.

COMPARATIVE EXAMPLE 1

At first, 2.86 g (10 mmol, 1 eq) of (±)-1,1'-bi-2-naphthol and 2.99 g (29.6 mmol, 2.96 eq) of triethylamine were added to 22 ml (2.2 ml/mmol) of methylene chloride, followed by stirring at room temperature for dissolution. The resulting solution (liquid) was cooled to −30° C. To the cooled solution (solid; stirring was not possible) 3.51 g (23.1 mmol, 2.31 eq) of trifluoromethanesulfonyl fluoride in liquid state were introduced at −30° C., followed by standing still for 1 hr at −30° C. With this, the solution (solid; stirring was not possible) was partially liquefied. Then, 120 ml of 1N hydrochloric acid were added to the reaction mixture at −30° C., followed by extraction with 50 ml of methylene chloride. The resulting extract was subjected to a liquid chromatography analysis using YMC-Pack ODS-AM312 under the conditions of $CH_3CN:H_2O=70:30$, 220 nm, column temperature: 30° C. and flow rate: 1 ml/min. With this, the conversion was found to be 23%.

EXAMPLE 1

At first, 2.86 g (10 mmol, 1 eq) of (±)-1,1'-bi-2-naphthol and 2.99 g (29.6 mmol, 2.96 eq) of triethylamine were added to 22 ml (2.2 ml/mmol) of acetonitrile, followed by stirring at room temperature for dissolution. Then, the same steps as those of comparative Example 1 were conducted. Similar to Comparative Example 1, the solution turned from liquid to solid (stirring was not possible) by the cooling to −30° C., and the solution (solid; stirring was not possible) was partially liquefied by the standing still for 1 hr at −30° C. The conversion was found to be 73%.

EXAMPLE 2

At first, 2.86 g (10 mmol, 1 eq) of (±)-1,1'-bi-2-naphthol and 2.99 g (29.6 mmol, 2.96 eq) of triethylamine were added to 22 ml (2.2 ml/mmol) of N,N-dimethylformamide, followed by stirring at room temperature for dissolution thereof. Then, the same steps as those of Comparative Example 1 were conducted except that the standing still for 1 hr was replaced with stirring for 1 hr. In fact, the solution was in a homogeneous liquid state (stirring was possible) even by the cooling to −30° C. and by the stirring for 1 hr. The conversion was found to be 85%.

COMPARATIVE EXAMPLE 2

The same steps as those of Comparative Example 1 were conducted until the introduction of trifluoromethanesulfonyl fluoride. Then, the resulting reaction mixture was allowed to stand still for 1 hr at 0° C. With this, the solution (solid; stirring was not possible) was partially liquefied. Then, 120 ml of 1N hydrochloric acid were added to the reaction mixture at 0° C. Then, the same steps as those of Comparative Example 1 were conducted. The conversion was found to be 73%.

EXAMPLE 3

At first, 2.86 g (10 mmol, 1 eq) of (±)-1,1'-bi-2-naphthol and 2.99 g (29.6 mmol, 2.96 eq) of triethylamine were added to 22 ml (2.2 ml/mmol) of acetonitrile, followed by stirring at room temperature for dissolution. Then, the same steps as those of Comparative Example 2 were conducted except that the standing still for 1 hr was replaced with stirring for 1 hr. In fact, the solution turned from liquid to solid by the cooling to −30° C., and the solution (solid; stirring was not possible) turned to a homogeneous liquid state (stirring was possible) by the stirring for 1 hr at 0° C. The conversion was found to be greater than 99%.

EXAMPLE 4

At first, 2.86 g (10 mmol, 1 eq) of (±)-1,1'-bi-2-naphthol and 2.99 g (29.6 mmol, 2.96 eq) of triethylamine were added to 22 ml (2.2 ml/mmol) of N,N-dimethylformamide, followed by stirring at room temperature for dissolution thereof. Then, the same steps as those of Comparative Example 2 were conducted except that the standing still for 1 hr was replaced with stirring for 1 hr. In fact, the solution was in a homogeneous liquid state even by the cooling to −30° C. and by the stirring for 1 hr at 0° C. The conversion was found to be greater than 99%.

EXAMPLE 5

At first, 28.6 g (100 mm/mmol, 1 eq) of (R)-(+)-1,1'-bi-2-naphthol and 29.3 g (290 mmol, 2.9 eq) of triethylamine were added to 200 ml (2 ml/mmol) of acetonitrile, followed by stirring at room temperature for dissolution. The resulting solution (liquid) was cooled to −50° C. To the cooled solution (suspension; stirring was possible) 39.5 g (260 mmol, 2.6 eq) of trifluoromethanesulfonyl fluoride in liquid state were introduced at −50° C. Then, the temperature of the resulting reaction mixture was increased to 0° C. by spending 1 hr with stirring. With this, the reaction mixture turned to a homogeneous liquid state (stirring was possible), and the internal pressure of the reaction vessel was about 0.03 MPa. Then, 400 ml of 1N hydrochloric acid were added to the reaction mixture at 0° C., followed by extraction with 600 ml of toluene. The resulting organic layer was concentrated, thereby obtaining a crude product with a quantitative yield. The crude product was subjected to a liquid chromatography analysis in the same manner as that of Comparative Example 1. With this, the conversion was found to be greater than 99%. The crude product was recrystallized from 110 ml of n-hexane, thereby obtaining 44.9 g of white crystals. The total yield was found to be 82%. The recrystallized product was found to be greater than 99% in liquid chromatography purity.

It was confirmed by specific rotation of the recrystallized product that the racemization of the binaphthol did not occur during the reaction. The specific rotation of the recrystallized product was as follows.

$[\alpha]^{26}D=-140.9°$ (c=1.044, CHCl$_3$)

The published value of specific rotation of the (S)-bistriflate compound is as follows.

$[\alpha]^{22}D=+142°$ (c=1.035, CHCl$_3$)

Other analytical data of the recrystallized product were the same as those of the published data of Organic Syntheses, Vol. 76, pp. 6–11.

The above-mentioned reaction steps were repeated except that (S)-(−)-1,1'-bi-2-naphthol was used in place of (R)-(+)-1,1'-bi-2-naphthol, thereby obtaining bistriflate of (S)-(−)-1,1'-bi-2-naphthol.

EXAMPLE 6

The same steps as those of Example 5 were repeated except that 200 ml (2 ml/mmol) of acetonitrile was replaced with 200 ml (2ml/mmol) of N,N-dimethylformamide. In fact, the solution was in a homogeneous liquid state (stirring was possible) even by the cooling to −50° C. When the temperature of the reaction mixture was increased to 0° C. with stirring, the reaction mixture was kept in a homogeneous liquid state (stirring was possible), and the internal pressure of the reaction vessel was about 0.03 MPa. The conversion was found to be greater than 99%. 43.1 g of white crystals were obtained by the recrystallization. The total yield was found to be 78%. The recrystallized product was found to be greater than 99% in liquid chromatography purity.

It was confirmed by specific rotation of the recrystallized product that the racemization of the binaphthol did not occur during the reaction. The specific rotation of the recrystallized product was as follows.

$[\alpha]^{26}D=-140.3°$ (c=1.010, CHCl$_3$)

Other analytical data of the recrystallized product were the same as those of the published data of Organic Syntheses, Vol. 76, pp. 6–11.

The above-mentioned reaction steps were repeated except that (S)-(−)-1,1'-bi-2-naphthol was used in place of (R)-(+)-1,1'-bi-2-naphthol, thereby obtaining bistriflate of (S)-(−)-1,1'-bi-2-naphthol.

The entire disclosure of Japanese Patent Application No. 11-307772 filed on Oct. 28, 1999, including specification, claims and summary, is incorporated herein by reference in its entirety.

What is claimed is:

1. A process for producing a binaphthol bistriflate represented by the formula (1), comprising reacting a binaphthol represented by the formula (2) with trifluoromethanesulfonyl fluoride, in a polar solvent, in the presence of an organic base.

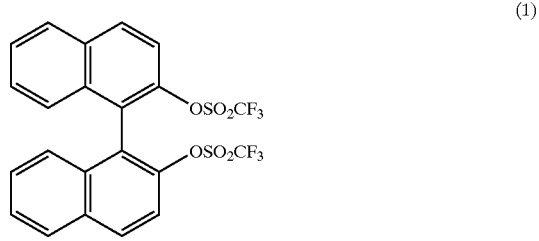

(1)

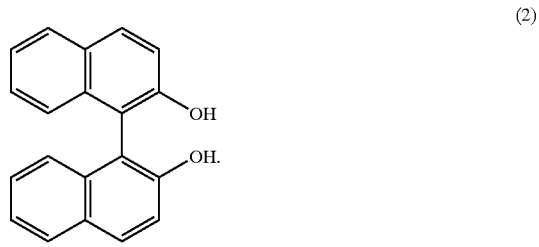

(2)

2. A process according to claim 1, wherein said polar solvent is at least one selected from the group consisting of N,N-dimethylformamide, N,N-diethylformamide, N,N-dimethylacetoamide, 1-methyl-2-pyrrolidinone, 1,3-dimethyl-2-imidazolidinone, hexamethylphosphoric triamide, dimethyl sulfoxide, acetonitrile, propionitrile, and benzonitrile.

3. A process according to claim 2, wherein said polar solvent is at least one selected from the group consisting of N,N-dimethylformamide, N,N-dimethylacetoamide, 1-methyl-2-pyrrolidinone, and acetonitrile.

4. A process according to claim 3, wherein said polar solvent is at least one selected from the group consisting of N,N-dimethylformamide and acetonitrile.

5. A process according to claim 1, wherein the reaction is conducted at a temperature of from −60 to 10° C.

6. A process according to claim 5, wherein the reaction is conducted at a temperature of from −50 to 0° C.

7. A process according to claim 5, wherein said polar solvent is in an amount sufficient for dissolving therein said binaphthol in an amount sufficient for conducting the reaction at said temperature.

8. A process according to claim 1, wherein said polar solvent is in an amount of 1–10 liters per mol of said binaphthol.

9. A process according to claim 8, wherein said polar solvent is in an amount of 1.5–5 liters per mol of said binaphthol.

10. A process according to claim 1, wherein said trifluoromethanesulfonyl fluoride is in an amount of at least 2 moles per mol of said binaphthol.

11. A process according to claim 10, wherein said trifluoromethanesulfonyl fluoride is in an amount of 2–10 moles per mol of said binaphthol.

12. A process according to claim 11, wherein said trifluoromethanesulfonyl fluoride is in an amount of 2–5 moles per mol of said binaphthol.

13. A process according to claim 1, wherein said organic base is at least one selected from the group consisting of trimethylamine, triethylamine, diisopropylethylamine, tri-n-propylamine, tri-n-butylamine, dimethyllaurylamine, dimethylaminopyridine, N,N-dimethylaniline, dimethylbenzylamine, 1,8-diazabicyclo(5,4,0)undecene-7, 1,4-diazabicyclo(2,2,2)octane, pyridine, 2,4,6-trimethylpyridine, pyrimidine, pyridazine, 3,5-lutidine, 2,6-lutidine, 2,4-lutidine, 2,5-lutidine, and 3,4-lutidine.

14. A process according to claim 13, wherein said organic base is at least one selected from the group consisting of trimethylamine, triethylamine, diisopropylethylamine, and tri-n-propylamine.

15. A process according to claim 14, wherein said organic base is triethylamine.

16. A process according to claim 1, wherein said organic base is in an amount of at lease 2 moles per mol of said binaphthol.

17. A process according to claim 16, wherein said organic base is in an amount of 2–10 moles per mol of said binaphthol.

18. A process according to claim 17, wherein said organic base is in an amount of 2–5 moles per mol of said binaphthol.

19. A process for producing a binaphthol bistriflate represented by the formula (1), comprising:

adding an organic base and a binaphthol represented by the formula (2) to a polar solvent to prepare a solution;

cooling said solution to a temperature at which trifluoromethanesulfonyl fluoride is in liquid state; and introducing trifluoromethanesulfonyl fluoride, which is in liquid state, into said solution, thereby reacting said binaphthol with said trifluoromethanesulfonyl fluoride

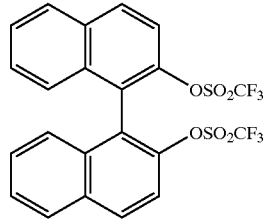

(1)

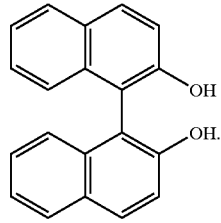

(2)

20. A process according to claim 19, wherein said temperature of said cooling is from −60 to −20° C.

* * * * *